United States Patent [19]

Arunachalam et al.

[11] Patent Number: 5,278,311

[45] Date of Patent: Jan. 11, 1994

[54] NONIONIC RADIOGRAPHIC CONTRAST AGENTS

[75] Inventors: Thangavel Arunachalam, Plainsboro; Ramachandran Ranganathan, Princeton, both of N.J.

[73] Assignee: E. R. Squibb & Sons, Inc., Princeton, N.J.

[21] Appl. No.: 893,621

[22] Filed: Jun. 5, 1992

[51] Int. Cl.$^5$ .................. C07D 211/36; C07D 207/09; C07D 333/16; C07D 307/12

[52] U.S. Cl. .................... 546/243; 546/247; 548/537; 549/72; 549/487

[58] Field of Search .................. 546/243, 247; 549/72, 549/487; 548/537

[56] References Cited

U.S. PATENT DOCUMENTS

| | | | |
|---|---|---|---|
| 2,750,393 | 6/1956 | Elpern | 260/308 |
| 2,776,241 | 1/1957 | Priewe et al. | 167/95 |
| 3,306,927 | 2/1967 | Larsen | 260/471 |
| 3,701,771 | 10/1972 | Almen et al. | 260/211 R |
| 3,883,535 | 5/1975 | Felder et al. | 260/293.76 |
| 3,890,318 | 6/1975 | Obendorf et al. | 260/247.2 |
| 3,925,412 | 12/1975 | Obendorf et al. | 260/326.47 |
| 4,001,298 | 1/1977 | Gries et al. | 260/471 |
| 4,066,743 | 1/1978 | Kneller | 424/5 |
| 4,250,113 | 2/1981 | Nordal et al. | 564/153 |
| 4,352,788 | 10/1982 | Felder et al. | 424/5 |
| 4,396,598 | 8/1983 | Lin | 424/5 |
| 4,845,235 | 7/1989 | Matumoto et al. | 548/550 |
| 4,962,204 | 10/1990 | Wambach . | |

FOREIGN PATENT DOCUMENTS

| | | |
|---|---|---|
| 0022744 | 1/1981 | European Pat. Off. . |
| 0026281 | 4/1981 | European Pat. Off. . |
| 0082803 | 6/1983 | European Pat. Off. . |
| 01005752 | 4/1984 | European Pat. Off. . |
| 0390242 | 10/1990 | European Pat. Off. . |
| 2726196 | 12/1977 | Fed. Rep. of Germany . |
| 3429949 | 2/1986 | Fed. Rep. of Germany . |
| 2007674 | 4/1969 | France . |
| 319226 | 12/1974 | Norway . |
| 1172654 | 12/1969 | United Kingdom . |
| WO91/09007 | 6/1991 | World Int. Prop. O. . |

OTHER PUBLICATIONS

Fumagalli, et al., "Radiopaque Contrast Media", *Pharmazie*, 30, H.2, pp. 78–79, Feb. 1975.

Stormorken et al., "Effect of Various Contrast Media on Coagulation, Fibrinolysis, and Platelet Function: An In Vitro and In Vivo Study", *Investigative Radiology*, vol. 21, Apr. 1986, pp. 348–354.

Mamon et al., "Biochemical Evidence for a Relative Lack of Inhibition of Thrombin Formation by Nonionic Contrast Media", *Radiology* 1991; 179:399–401.

G. B. Hoey et al., "Chemistry of X-Ray Contrast Media" pp. 23–125. 1984.

Laerum et al., "Postphlebographic Thrombosis", *Diagnostic Radiology*, Sep. 1981, pp. 651–654.

*Primary Examiner*—C. Warren Ivy
*Assistant Examiner*—A. Owens
*Attorney, Agent, or Firm*—Furman, Jr. Theodore R.; Suzanne E. Babajko

[57] ABSTRACT

Novel nonionic contrast agents of the formula

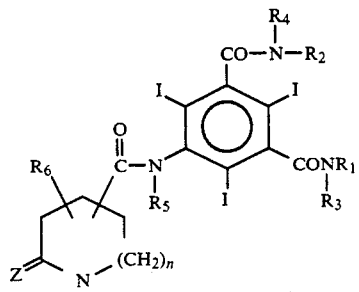

or dimers of the formula

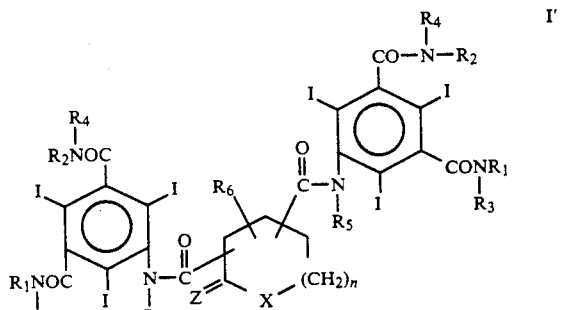

are disclosed where X, Z and $R_1$–$R_5$ are as defined herein.

6 Claims, No Drawings

NONIONIC RADIOGRAPHIC CONTRAST AGENTS

BACKGROUND OF THE INVENTION

This invention relates to new nonionic radiographic contrast agents having desirable water solubility and low osmolality properties. These new compounds are derivatives of the 5-amino-2,4,6-triiodo-1,3, benzenedicarboxylic acid moiety, wherein the 5 amino nitrogen atom is part of a 4,5 or 6-membered heterocyclic ring.

DESCRIPTION OF THE PRIOR ART

Ionic contrast agents that contain a heterocyclic ring and an iodobenzene moiety have been reported in the literature. For instance Iodophthalein is disclosed in Amer. J. Pharm., 100, 374 (1928). U.S. Pat. No. 2,776,241 discloses dimeric compounds with heterocyclic bridges. U.S. Pat. No. 3,306,927 discloses heterocycles as counter ions. U.S. Pat. No. 2,750,393 discloses ionic cholecystopaques. British Patent 1,191,015 discloses 3,5-diamino-benzoic acids. U.S. Pat. No. 4,066,743 discloses 5-amino-isophthalic acids. U.S. Pat. No. 4,250,113 discloses 3- aminobenzoic acids.

Non-ionic contrast agents having a heterocyclic ring including sugar ethers, acyl amides or aminosugars and reversed amides from keto-sugars have been disclosed in the prior art.

EP (431,838) discloses contrast agents of the formula

[Structure with $R_4$, $R_2$, $R_1$, $R_3$, $R_5$, $R_6$, $Y(CH_2)_m$—$CH_2$]

wherein Y is a single bond, —CH$_2$—CH$_2$—, —CH$_2$O—, —OCH$_2$—, —N—CH$_2$—, —CH$_2$—N—C—, —CH$_2$N—, —CH$_2$—, —CH$_2$—CH$_2$—CH$_2$—, —O— or —N.

SUMMARY OF THE INVENTION

The new contrast agents of this invention have the formula

[Structure I with $R_4$, $R_2$, $R_1$, $R_3$, $R_5$, $R_6$, Z, X, $(CH_2)_n$]

or dimers of the formula

[Structure I' dimer with $R_4$, $R_2$, $R_1$, $R_3$, $R_5$, $R_6$, Z, X, $(CH_2)_n$]

wherein X is selected from —O—, —S—, $$-\underset{\underset{\text{alkyl}}{|}}{\overset{|}{N}}-\overset{|}{\underset{|}{C}}=O\ ,\quad -\underset{\underset{\text{hydroxyalkyl}}{|}}{\overset{|}{N}}-\overset{|}{\underset{|}{C}}=O\quad \text{or}\quad -\underset{R}{\overset{|}{N}}-;$$

Z is H,H, alkyl or hydroxyalkyl when X is other than $$-\underset{R}{\overset{|}{N}}-;$$

or

Z is O when X is $$-\underset{R}{\overset{|}{N}}-;$$

R is hydrogen, alkyl or hydroxyalkyl;

$R_1$ and $R_2$ are independently selected from H, alkyl, hydroxyalkyl;

$R_3$, $R_4$ and $R_5$ are independently selected from hydrogen, alkyl, or hydroxyalkyl; $R_6$ is alkyl, O—alkyl, CH$_2$O—alkyl, —CH$_2$CH$_2$OH, CH$_2$OH, OH, hydrogen or I; and n=0 or 1; and further wherein $R_1$-$R_5$ in one triiodinated phenyl group can be the same as or different from $R_1$-$R_5$ in the other triiodinated phenyl group in the dimers of formula II. The term alkyl refers to straight or branched chain groups of one to six carbon atoms such as methyl, ethyl and propyl.

The term hydroxyalkyl refers to such alkyl groups substituted with one or more —OH groups. Preferred hydroxyalkyl groups include $$HOCH_2-\underset{\underset{OH}{|}}{\overset{\overset{H}{|}}{C}}-CH_2-,\quad CH\underset{CH_2OH}{\overset{CH_2OH}{<}}\ ,\quad -CH_2CH_2OH,$$

$$\begin{array}{c}CH_2OH\\|\\-CH\\|\\H-C-OH\\|\\H-C-OH,\\|\\H\end{array}\quad \text{or}\quad \begin{array}{c}CH_2OH\\|\\-CH\\|\\HO-C-H\\|\\CH_2OH\end{array}.$$

DESCRIPTION OF THE PREFERRED EMBODIMENTS

The compounds of formula I all have a molecular weight of from 780 to 835. They have from four to six hydroxy groups per monomeric unit. They all have one or two tertiary nitrogen preferred. This unique set of parameters allows for new non-ionic contrast agents which are expected to exhibit low toxicity, high chemical stability, ease of chemical synthesis, low viscosity and low osmolality of concentrated aqueous solutions of the contrast agent.

The following groups substituted and unsubstituted are representative of the heterocycles connected to the 5-position of the benzene ring in Formula I:

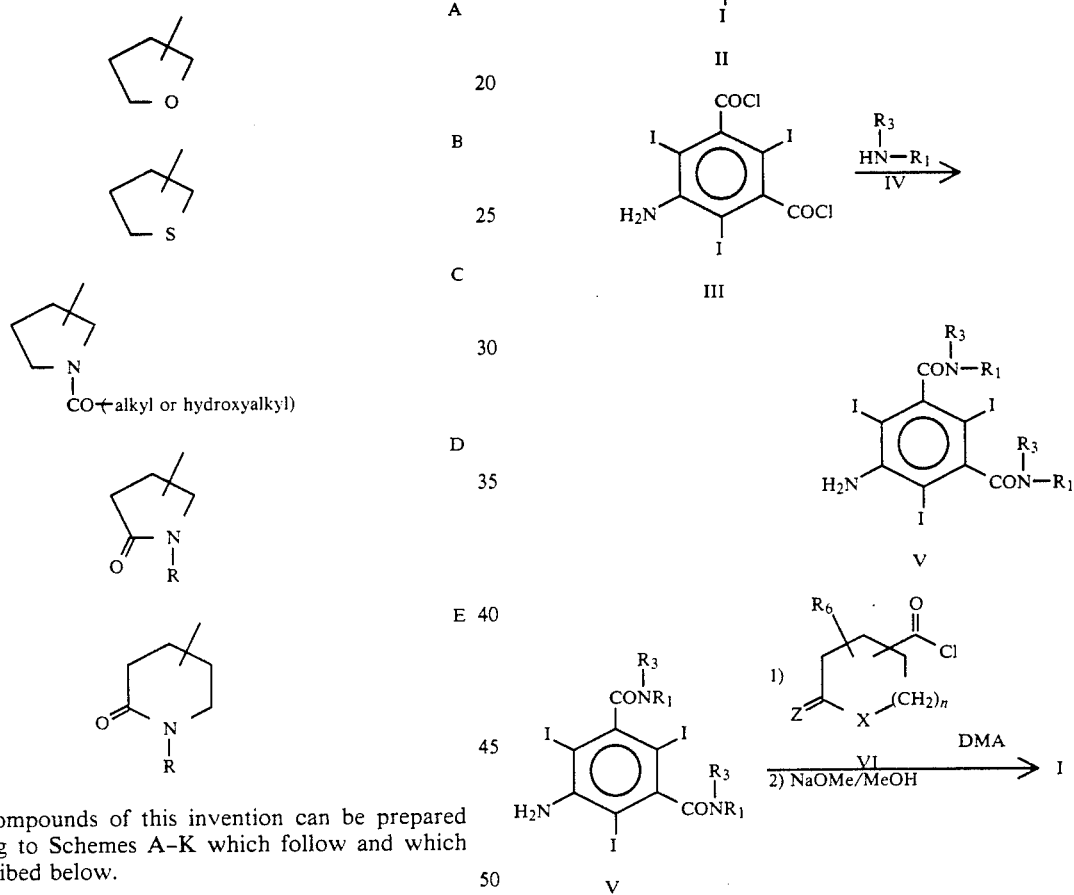

The compounds of this invention can be prepared according to Schemes A-K which follow and which are described below.

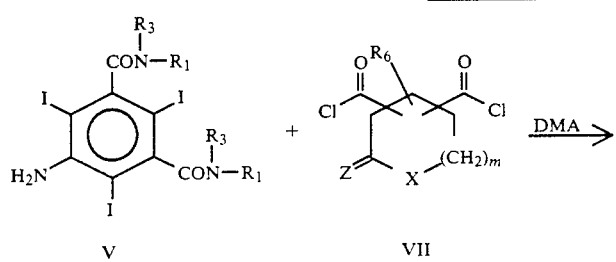

5,278,311
-continued
Scheme B
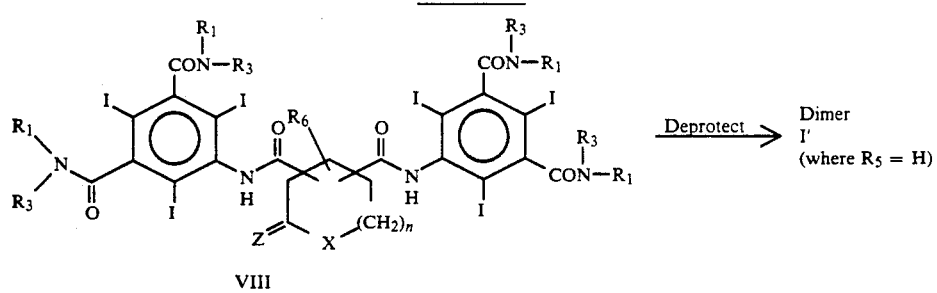
Scheme C
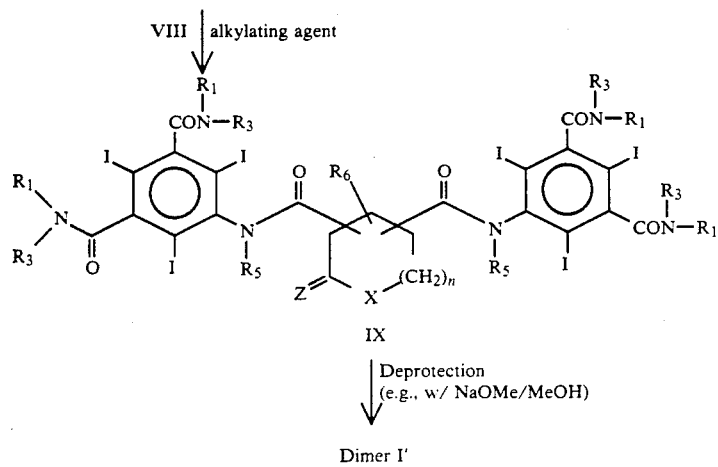
Scheme D
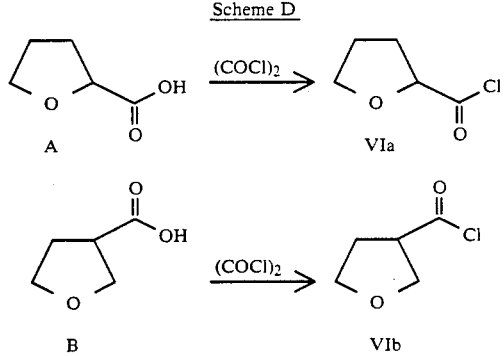
-continued
Scheme E
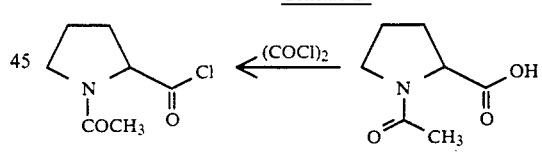
Scheme E
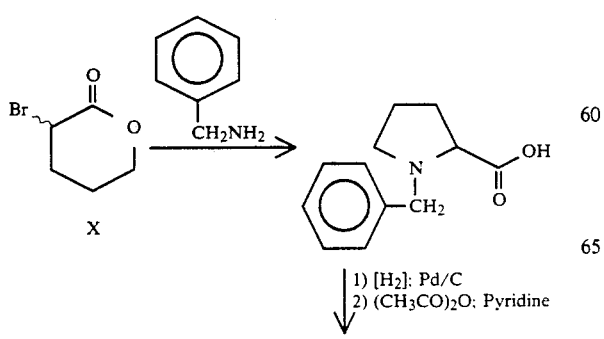
1) [H$_2$]: Pd/C
2) (CH$_3$CO)$_2$O; Pyridine
Scheme F
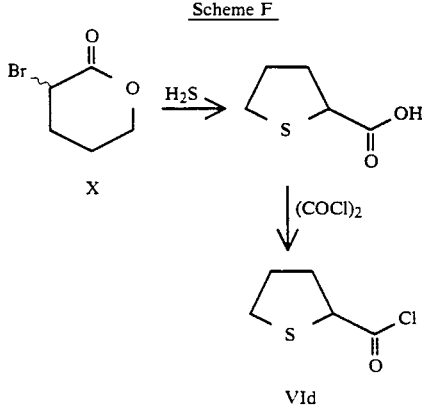

Scheme G

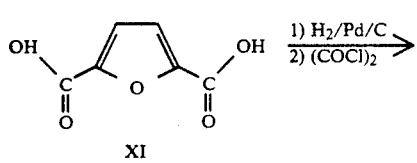

Scheme H

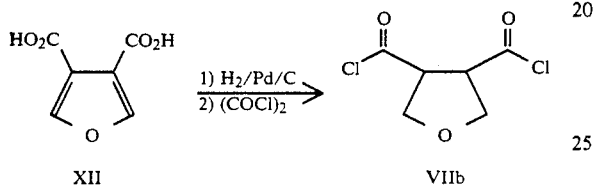

Scheme I

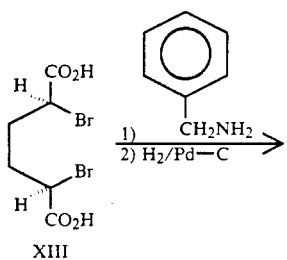

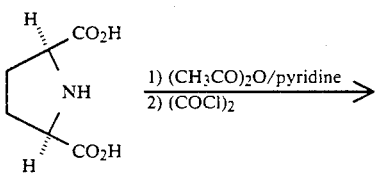

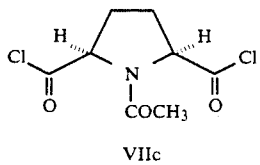

Scheme J

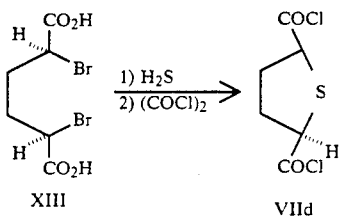

Scheme K

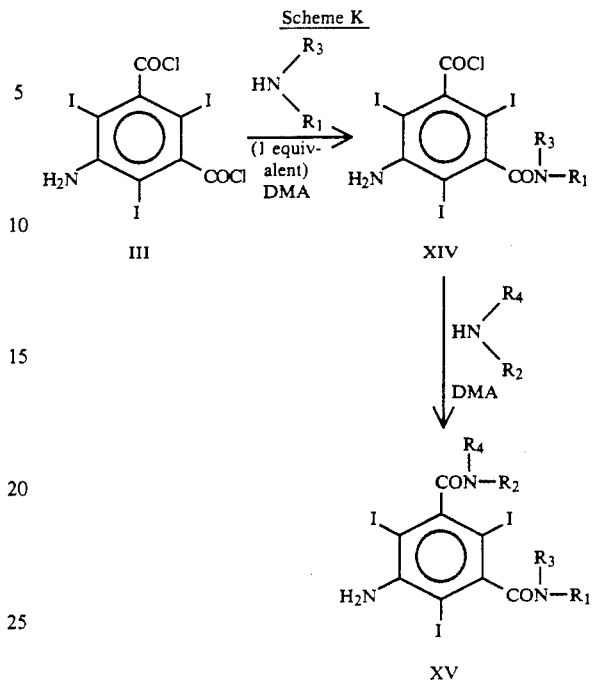

The compounds of the present invention, wherein

is the same as

can be prepared according to Scheme A.

Compound IA which is commercially available is iodinated with a compound such as potassium iododichloride in dilute hydrochloric acid solution to obtain 5-amino-2,4,6,-triiodo-1,3-benzenedicarboxylic acid (II). Compound II is chlorinated with purified thionyl chloride to obtain the corresponding bis-chloride (III). Compound III is then amidated with the desired intermediate of formula IV to obtain the isophthalamide V. The hydroxy groups in any of $R_1$-$R_4$ in compound V are protected, for example, by selective O-acylating (e.g. treatment with acetic anhydride in pyridine). Thereafter, compound V is reacted with the carbonyl chloride VI in an activating solvent, such as N,N-dimethylacetamide and then deacetylated, to provide the products of formula I. Removal of acetate protecting groups can be carried out by known techniques, such as by treatment with NaOMe and methanol.

The dimer I' is prepared analogously, as shown in Scheme B, by reacting compound V with a bifunctional bis-carbonyl chloride VII to obtain the protected dimers VIII. Removal of acetate protecting groups can be carried out as above to obtain the dimer I' where $R_5$=H.

Alternatively, the protected dimer can be alkylated by treatment with alkylating agents, as shown in Scheme C, such as methyl iodide, 2-bromoethanol, 3-chloropropane-1,2-diol and the like, to obtain the bis-N- alkylated product IX wherein $R_5$ is methyl, hydroxyethyl, or 2,3-dihydroxypropyl etc. Removal of the acetate protecting groups affords the N,N'-bis-alkylated dimer I', wherein $R_5$ is other than H.

The compound of formula VI, wherein $X=O$ and $n=$ zero, is made by treating commercially available tetrahydro-2-furoic acid (A) or tetrahydro-3-furoic acid (B) with oxalyl chloride to obtain the corresponding acid chlorides VIa or VIb, as shown in Scheme D. The compounds of formula VI, wherein $X=NHCOCH_3$, $Z=H,H$ and $n=$ zero, VIc are made from commercially available α-bromo-δ-valero-lactone X as shown in Scheme E. The compound of formula VI wherein $X=S$, $Z=H,H$ and $n=$ zero (VId), is made from α-bromo-δ-valero-lactone X as shown in Scheme F. The higher homologs wherein $n>1$ is made by analogous methods. The compound of formula VII, wherein $X=O$, $n=$ zero and the COCl functions are at carbon atoms 2 and 5, is made from commercially available furan-2,5-dicarboxylic acid (XI) as shown in Scheme G. In a similar manner starting from furan-3,4-dicarboxylic acid (XII), the compound of formula VII wherein $X=O$, $n=$ zero, and the COCl functions are at carbon atoms 3 and 4, is prepared as shown in Scheme H.

The compound of formula VII wherein $X=NHCOCH_3$, $n=$ zero and the COCl functions are at carbon atoms 2 and 5, is made from commercially available meso-2,5-dibromoadipic acid (XIII) as shown in Scheme I. Similarly, by reacting meso-2,5-dibromoadipic acid (XIII) with $H_2S$, the S analog of structure VII, wherein $X=S$, $n=$ zero, and the COCl functions at carbon atoms 2 and 5 is made as shown in Scheme J.

Compounds of formula VI where X is NR and Z is O can be readily prepared by treating 2-pyrrolidine-5-carboxylic acid with $SOCl_2$ and $(COCl)_2$. Compounds of formula VII where X is NR and Z is O can be prepared by treating 2-pyrrolidine-5-carboxylic acid as described by F. Effenberger et al., *J. Org. Chem.* 55, 3064 (1990) to provide the diacid which can thereafter be converted to the bis-acid chloride VII by treatment with $SOCl_2$ or $COCl_2$.

Compounds of formula I where

does not equal

can be prepared as shown in Scheme K. The bis-chloride III is treated in DMA with one equivalent of the first amine $HNR_1R_3$ in DMA under mild conditions, preferably between 0°–20° to obtain the mono-amide XIV, which is then treated with the second amine $HNR_2R_4$ in DMA to provide the unsymmetrical bis-amide XV. The mixed amide XV is then processed as described for the symmetrical bis-amide V to obtain the corresponding desired compounds I and I'

The compounds of the invention are suitable for use in most fields of application in which water soluble radiopaque compounds are necessary, such as vasography, urography, arthrography, and for the visualization of body cavities containing cerebrospinal fluid. When formulated with addition agents which increase the viscosity of the aqueous solutions, they may be employed to advantage for bronchography and hysterosalipingography.

The radio-opaque compounds of the invention are particularly useful as active ingredients of aqueous compositions for visualization of the cardiovascular system and for cerebral angiography. Because of their non-ionic nature, they are suited for visualization of body cavities containing spinocerebral liquor such as in radiculography, ventriculography and myelography.

Aqueous compositions for the applications indicated above may be formulated to contain a single compound of the invention, or more than one compound of the invention, if the individual compounds are very pure.

The radio-opaque compositions of the invention are aqueous solutions containing 15 g and more of the compounds per 100 ml, equivalent to 50 to approximately 500 mg iodine per ml. The more concentrated solutions are generally preferred, and they are applied in a manner generally known and selected according to the body cavity which it is intended to visualize. In vasography, the solutions are injected or infused into the vessels, particularly the blood vessels. Intravenous injection is resorted to in urography. For myelography and radiculography, the solutions are instilled after lumbar or suoccipital puncture. The amounts of solution necessary generally are 5 to 15 ml for myelography, 3 to 5 ml for radiculography, and 1 to 2 ml in ventriculography.

The X-ray contrast compositions containing the compounds of the invention as active ingredients are prepared in a very simple manner since no salt-forming or solubilizing ingredients are needed. Any one of the compounds of Examples 1–6 may be dissolved under sterile conditions in the desired amount of double-distilled water, and the solution so obtained is ready to be received in vials and sterilized. The compounds are not decomposed at sterilizing temperatures during the usual sterilizing periods (30 minutes at 120° C. or 60 minutes at 100° C.).

The new heterocycle based non-ionic contrast agents described herein have improved features not present in currently available contrast agents. Their superior stability characteristic, eliminates the need to use organic buffers or carbon dioxide saturation during sterilization of their formulations by autoclaving.

The new heterocycle based non-ionic contrast agents described herein are found to have excellent properties as to tolerance, water solubility, stability, osmolality, viscosity and the like, factors important in angiography and urography.

Preferred compounds in accordance with the present invention are those of formula I wherein X is oxygen and $n=O$.

The most preferred compounds are those of formula I wherein
X is oxygen;
$Z=H,H$;
$n=O$;
$R_1$ and $R_2$ are

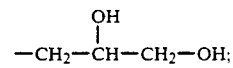

and
$R_3$ and $R_4$ are each hydrogen.

EXAMPLE 1

N,N¹-bis(2,3-dihydroxypropyl)-2,4,6-triodo-5[{(tetrahydro-2-furanyl)carbonyl}amino]-1,3-benzenedicarboxamide

A. Tetrahydro-2-furancarbonyl chloride

Oxalyl chloride (6.36 g, 50 mmol) was added dropwise under a nitrogen atmosphere to tetrahydro-2-furoic acid (2.32 g, 20 mmol) with gentle stirring. After the addition, the mixture was stirred at room temperature for 15 hours. Excess oxalyl chloride was distilled off, and the residue was then distilled in vacuo to obtain pure title A compound (2.42 g) as a colorless liquid. bp: 75°-76° (23 mm.Hg)

B. 5-Amino-N,N'-bis[2,3-bis(acetyloxy)propyl]-2,4,6-triiodo-1,3-benzenedicarboxamide To a solution of 5-amino-2,4,6-triiodo-1,3-benzenedicarbonyl dichloride (34.00 g, 0.057 mole; which can be prepared as described in U.S. Pat. No. 4,001,322) in anhydrous dimethylacetamide (200 ml), was added 1-amino-2,3-propanediol (22.00 g, 0.24 mole) in dimethylacetamid (50 ml) over a period of 30 minutes and the solution was stirred at room temperature. The progress of the reaction was followed by TLC and it was found to have gone to completion in 16 hours. Dimethylacetamide was removed in vacuo at 50°-60°. The syrupy residue, containing the bis-amide, was subjected to selective O-acetylation, without any further purification, by dissolving it in pyridine (200 ml) and treating with acetic anhydride (100 g, 1 mole) over a period of 30 minutes maintaining the temperature below 50° C. When the addition was over, the reaction mixture was allowed to come to room temperature and was stirred for 6 hours. Water (20 ml) was added, in order to decompose the excess of acetic anhydride. Pyridine was then removed in a rotary evaporator at 40°-50°. Toluene (100 ml) was added and the solvent distilled off to remove any remaining traces of pyridine, by azeotropic distillation. The product was redissolved in ethyl acetate (300 ml) and then washed with water (2×100 ml), 1N hydrochloric acid (2×100 ml), followed by water (2×100 ml), saturated aqueous sodium bicarbonate (2×100 ml), water (2×100 ml) and brine (100 ml). The organic layer was dried and the solvent removed, to obtain the crude product as a pale orange syrup (71.00 g).

Impurities were removed by column chromatography over silica gel (500 g, ratio 1:7), using a mixture of ethyl acetate (75%) and hexane (25%), as the eluent. The fractions containing the pure product, as determined by silica gel TLC, were combined and the solvents removed to obtain the title B compound as an off-white glassy solid (47.00 g).

Elemental analysis calc'd $C_{22}H_{26}I_3N_3O_{10}$: C, 30.38; H, 3.03; I, 43.38; N, 4.79; Found: C, 30.85; H, 2.93; I, 43.77; N, 4.75.

C. N,N¹-Bis[2,3-bis(acetyloxy)propyl]-2,4,6-triodo-5[{(tetrahydro-2-furanyl)carbonyl}-amino]-1.3-benzenedicarboxamide To a stirred solution of the title B compound (8.73 g, 10 mmol) in N,N-dimethylacetamide (30 mL), was added in drops the title A compound (1.8 g, 13 mmol) at 0°-5°. After the addition, the mixture was stirred at 0°-5° for 0.5 hours, then at room temperature for 20 hours. Nitrogen gas was purged through the solution for 0.25 hours, and the DMA was removed in vacuo. The residue was dissolved in ethyl acetate (200 mL), and the solution was washed successively with cold aq. sodium bicarbonate (2×50 mL), water 2×50 mL) and saturated sodium chloride (2×50 mL). After drying over sodium sulfate, the solvent was removed in vacuo to obtain the crude furanilide as an off-white foamy material (9.27 g). The crude product (7.2 g), upon purification by column chromatography over silica gel furnished the title C compound. mp: 101°-104°

Element analysis: Anal. Calcd for $C_{27}H_{32}I_3N_3O_{12}$ (971.28): C, 33.39; H, 3.32; I, 39.20; N, 4.33; O, 19.77. Found: C, 33.39; H, 3.27; I, 38.78; N, 4.26.

D. N,N¹-bis(2,3-dihydroxypropyl)-2,4,6-triodo-5[{(tetrahydro-2-furanyl)carbonyl}amino]-1,3-benzenedicarboxamide To a solution of the title C compound (4.85 g, 5 mmol) in anhydrous methanol (50 mL), was added a solution of sodium methoxide in methanol (prepared by reacting 20 mg of sodium with 2 mL of methanol). The mixture was stirred for 4 hours at room temperature. The solution was adjusted to pH 7 by the addition of AG 50W-X8 (H+form). The resin was filtered off, and the filtrate concentrated in vacuo to give 2- Iofuranol-A as a white solid (4.01 g, yield 99.8%, purity 99.5%). The material was purified by low pressure reverse phase column chromatography over CHP-20 resin. The resulting white solid was redissolved in water (100 mL) and lyophilized to obtain the title compound (3.51 g, yield 87.4%, purity 100%) as a white fluffy solid; m.p. 202°-204° C. (softens at 183°-186°)

Elemental analysis calc'd for $C_{19}H_{24}I_3N_3O_8.0.61$ $H_2O$ (814.2): C, 28.03; H, 3.12; I, 46.76; N, 5.16; O, 16.93. Found: C, 28.11; H, 2.99; I, 46.46; N, 5.10; $H_2O$, 1.36%.

What is claimed is:

1. A compound of the formula

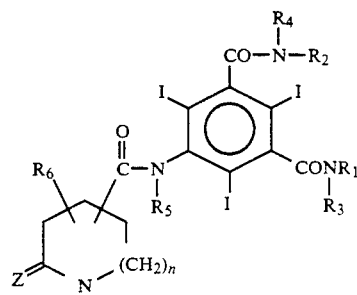

I or dimers of the formula

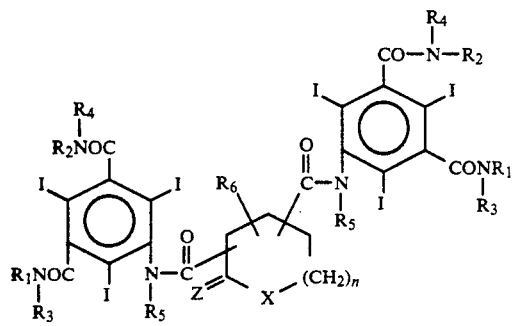

wherein X is selected from —O—, —S—,

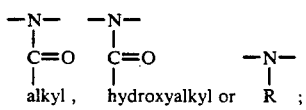

Z is H,H, alkyl or hydroxyalkyl when X is other than

or
Z is O when X is

R is hydrogen, alkyl or hydroxyalkyl;
$R_1$ and $R_2$ are independently selected from H, alkyl, hydroxyalkyl;
$R_3$, $R_4$ and $R_5$ are independently selected from hydrogen, alkyl, or hydroxyalkyl; $R_6$ is alkyl, O-alkyl, $CH_2O$—alkyl, —$CH_2CH_2OH$, $CH_2OH$, OH, Hydrogen or I; and n=0 or 1; and further wherein $R_1$-$R_5$ in one triiodinated phenyl group can be the same as or different from $R_1$-$R_5$ in the other triiodinated phenyl group in the dimers of formula I', and wherein the term alkyl refers to straight or branched chain groups of one to six carbons and wherein hydroxyalkyl refers to such groups having one or more hydroxy moieties.

2. A compound of claim 1 wherein hydroxyalkyl is selected from

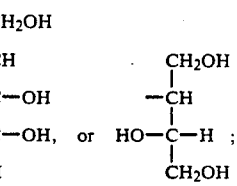

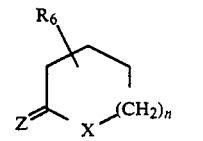

3. A compound of claim 1 wherein the

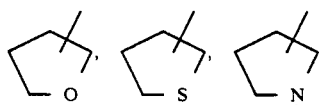

group is selected from

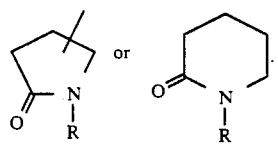

4. A compound of claim 1 wherein X is oxygen and n=O.

5. A compound of claim 1 wherein X=oxygen n=O, Z is H,H;
$R_1$ and $R_2$ are

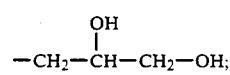

and
$R_3$ and $R_4$ are each hydrogen.

6. A compound of claim 1 bearing the name N,N¹ bis (2,3-dihydroxypropyl)-2,4,6- triodo-5[{(tetrahydro-2-furanyl)carbonyl}amino]-1,3,-benzenedicarboxamide.

* * * * *